US 8,094,296 B2

(12) United States Patent
Paavola

(10) Patent No.: US 8,094,296 B2
(45) Date of Patent: Jan. 10, 2012

(54) OPTICAL INSPECTION OF SURFACES OPEN TO DIFFERENT DIRECTIONS IN A PIECE OF MATERIAL

(75) Inventor: Jyri Paavola, Tuusula (FI)

(73) Assignee: Oy Ekspansio Engineering Limited, Kerava (FI)

( * ) Notice: Subject to any disclaimer, the term of this patent is extended or adjusted under 35 U.S.C. 154(b) by 807 days.

(21) Appl. No.: 11/597,046

(22) PCT Filed: Apr. 12, 2005

(86) PCT No.: PCT/FI2005/000182
§ 371 (c)(1),
(2), (4) Date: Jul. 16, 2008

(87) PCT Pub. No.: WO2005/111538
PCT Pub. Date: Nov. 24, 2005

(65) Prior Publication Data
US 2009/0002694 A1    Jan. 1, 2009

(30) Foreign Application Priority Data
May 18, 2004    (FI) ..................................... 20040694

(51) Int. Cl.
*G01N 21/00* (2006.01)
(52) U.S. Cl. .................................................. 356/237.2
(58) Field of Classification Search ............... 356/237.2
See application file for complete search history.

(56) References Cited

U.S. PATENT DOCUMENTS

| 5,910,844 A * | 6/1999 | Phillips et al. ................ 356/614 |
| 6,141,040 A | 10/2000 | Toh |
| 6,813,016 B2 * | 11/2004 | Quist ......................... 356/237.1 |
| 2003/0174318 A1 | 9/2003 | Quist |

FOREIGN PATENT DOCUMENTS

| DE | 4104501 | 9/1991 |
| DE | 19716468 | 10/1998 |
| EP | 1089106 | 4/2001 |
| JP | 2092168 | 3/1990 |
| JP | 10221036 | 8/1998 |
| WO | WO 9424516 | 10/1994 |
| WO | WO 0189204 | 11/2001 |

* cited by examiner

*Primary Examiner* — Roy M Punnoose
(74) *Attorney, Agent, or Firm* — Alfred A. Fressola; Ware, Fressola, Van Der Sluys & Adolphson LLP

(57) ABSTRACT

The invention relates to a device for optical inspection of the open surfaces (19 of objects from at least two different viewing directions (P1, P2). The device comprises a telecentric imaging unit (11 or 12, an angle mirror (13) and auxiliary mirrors (8) within the area (K) of the telecentric imaging unit, between this and the object. The object is placed between the arms (3a, 3b) of the angle mirror (13) and the telecentric imaging unit is directed towards the combination of object and angle mirror. The auxiliary mirrors (8) have been oriented and positioned at intervals from the telecentric imaging unit such that the differences of distance of the viewing directions (P1 and/or P2 and/or P3 and/or P4) via the two arms (3a and 3b) of the angle mirror or via one arm (3a tai 3b) or not via the arms are compensated as they pass via the auxiliary mirrors.

18 Claims, 6 Drawing Sheets

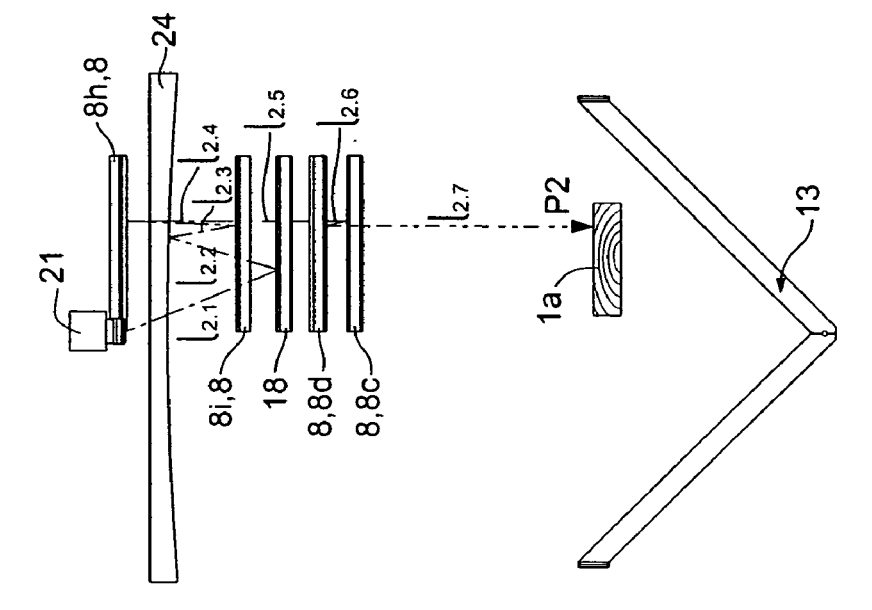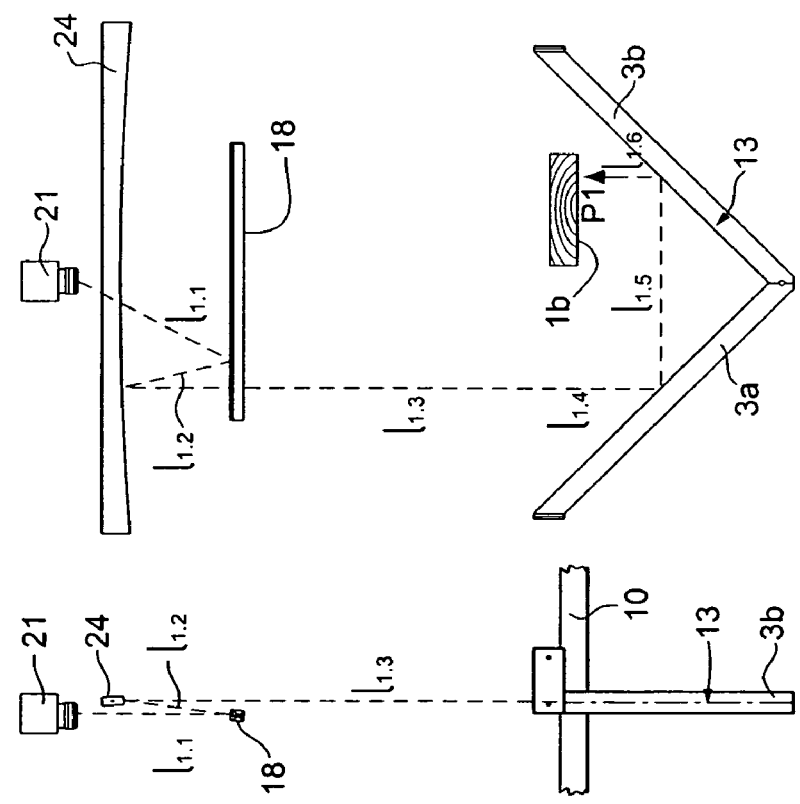

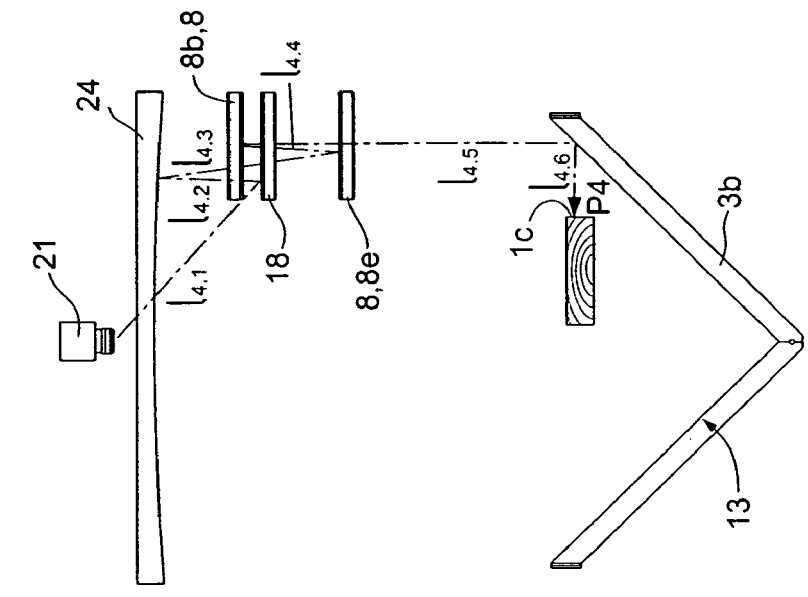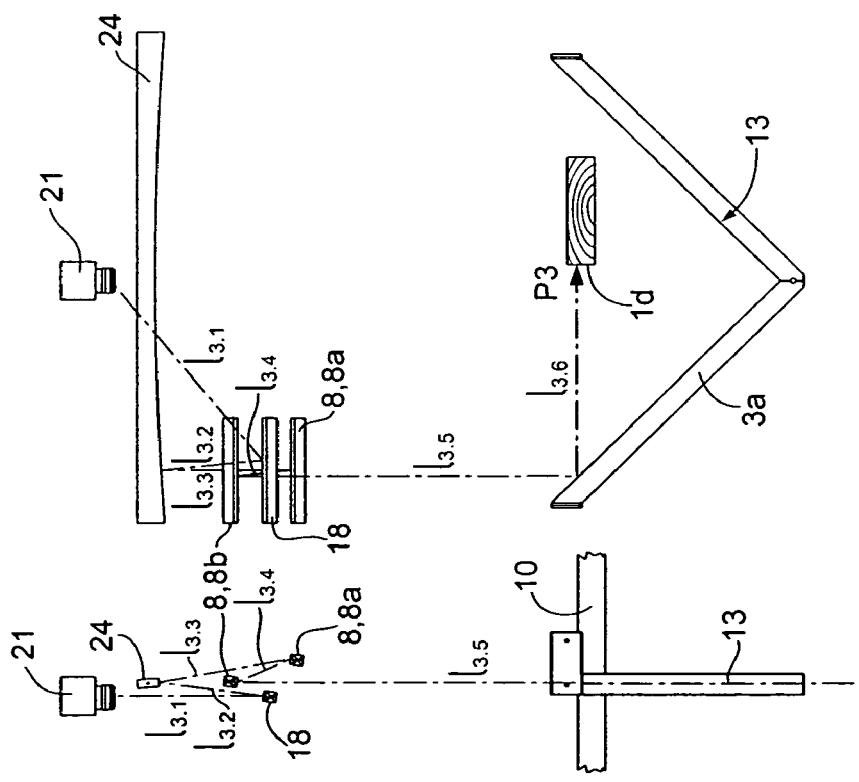
FIG. 6A  FIG. 6B
FIG. 5A  FIG. 5B

OPTICAL INSPECTION OF SURFACES OPEN TO DIFFERENT DIRECTIONS IN A PIECE OF MATERIAL

CROSS REFERENCE TO RELATED APPLICATIONS

This application is for entry into the U.S. national phase under §371 for International Application No. PCT/FI05/000182 having an international filing date of Apr. 12, 2005, and from which priority is claimed under all applicable sections of Title 35 of the United States Code including, but not limited to, Sections 120, 363 and 365(c) and which in turn claims Priority under Section 119 to Finnish Patent Application No. 20040694 which was filed on May 18, 2004.

TECHNICAL FIELD

The invention relates to a device for optical inspection of open surfaces of objects from at least two different viewing directions, the device comprising: illuminating means (light or radiation source) for illuminating the open surfaces of the objects; sensor means (sensor) for detecting the light intensity reflected by different locations of the open surfaces of the objects and for converting the light into electronic form.

BACKGROUND OF THE INVENTION

A typical optical inspection apparatus consists of a radiation source and a camera composed of an objective and an image plane. The image generated by the objective on the image plane can be inspected and stored e.g. by means of a CCD cell or a CMOS array, which converts the image into an electric signal in a known manner. Such a cell consists of light-sensitive elements disposed as a matrix, e.g. 256×256 elements or pixels. In this case, the properties of the camera resemble those of an ordinary photographing camera. The image plane formed of pixels may also have e.g. the shape 1024×1, and this is then a "linear camera". This text refers to a camera of the type described above as an electronic camera and it can be used for taking moving pictures or, if desired, also still pictures—in other connections their established name is "video camera" or "digital camera". Conventional camera optics views the object in different ways depending on the location of the object in the measurement area. At the optical axis of the objective, i.e. the central area of the object, the camera views the object at right angles, and at its edges at an oblique angle, which is larger the greater the distance from the optical axis. This is called the central perspective, which causes detrimental imaging errors for the measurement of the object and quality control in general, and these errors can be corrected by means of telecentric optics. In that case, all the beams from the object arrive in parallel with the optical axis and all the locations of the object are viewed in the same plane perspective. In telecentric objectives, the lens or concave mirror closest to the object should have a width equalling at least the object, and this results in heavy and bulky optical equipment consisting of ordinary lenses and/or mirrors. EP 1 089 106 discloses a relatively light and simple solution to these problems. The telecentric design of this reference uses a strip-like planar parabolic mirror, the aperture of the objective proper being located in the area of the focal plane of the mirror. This objective proper, in turn, is integrated in a non-telecentric camera, which generates an image on a light-sensitive image plane.

In many cases, it is necessary to measure and/or inspect the object also from other directions than one specific direction. Thus, for instance, it may be necessary to monitor sawn timber from the direction of two opposite faces or from the directions of all four faces. This can obviously be done by means of four devices directed towards the upper surface, lower surface and lateral surfaces of the object, but this incurs high equipment costs. Another option is turning the object and running it through the imaging area of a telecentric imaging unit four times. Firstly, such an arrangement is slow in terms of production and secondly, mutual positioning of the image data obtained on different sides of the object is problematic. WO 94/24516 depicts an arrangement for measuring the width of a moving object by using two parabolic mirrors in connection with one camera, together with an elongated light source providing background light. For measuring the thickness of the object, laser included in the arrangement and a second camera are used, and if necessary, a second laser and a third camera. This arrangement only allows for measurement of the boundary dimensions of the object in different projections.

DE 41 04 501, again, explains an arrangement for determining the sapwood side and the heartwood side of two even surfaces of sawn timber, such as planks and boards. The reference makes a difference between these opposite sides by utilising their different grain densities, i.e. growth ring densities. In order to determine these different grain densities, the reference suggests passing the timber body between at least one pair of sensors, with the sensors disposed opposite each other. These at least two sensors consist of a transmitter and a receiver operating in the range of visible light or infrared light. The sensors identify the growth rings on the basis of the different light reflectivity of adjacent locations on the timber body, and these initial data of the opposite sensors regarding differences in reflection density are fed into a comparator in the reference, the comparator calculating by means of not represented software which of the two opposite sides is sapwood and heartwood, respectively. The inherent structure of the sensors has not been described in any way, however, the figures of the reference and the definition "transceiver" allow the conclusion that the sensor detects only one pixel at a time, without any optics proper. The reference does not specify whether the measurement is based on average reflection densities of larger areas of the object—in the case of a large-sized pixel—or on the reflection density provided by transversely movable sensors or a plurality of sensors—in the case of a small-sized pixel. In other words, the arrangement of this reference allows observation of two surfaces of the object, however, the number of sensors is at least equal to the number of inspected surfaces. The reference does not indicate the manner of inspecting the entire area of even one surface of the object.

SUMMARY OF THE INVENTION

Hence the invention has the purpose of providing an arrangement allowing inspection of the surface of an object in all its cross-sectional directions by optical means, i.e. an electronic camera. This means that the invention enables imaging and inspection of the upper surface, lower surface and the lateral surfaces of the object, in other words, the object is then usually viewed from four mutually perpendicular directions, which are typically in the same plane, but at least in mutually parallel planes. Depending on the shape of the object, it is, of course, permissible to optionally image and inspect it from only three corresponding directions. The second purpose of the invention is to provide an arrangement allowing the imaging inspection of the type described above to be carried out with a minimum number of cameras in order to keep the expenditures low. The third purpose of the invention is to provide an arrangement allowing the imaging inspection of the type above to be performed at surfaces of a movable object open to different directions so that all the surfaces of say, elongated bodies, are imaged and inspected if desired. The fourth purpose of the invention is to provide an arrangement allowing the imaging inspection to be applied to the analysis of all types of errors and properties of the object. This means that the arrangement proper should not restrict the features of the object to be determined. The invention has the further purpose of providing such an arrangement allowing imaging inspection to be carried out without repetition and using an apparatus devoid of moving parts.

The problems explained above are resolved and the purposes defined above are achieved with the arrangement in accordance with the invention.

One of the chief advantages of the invention is that the arrangement of the invention allows imaging of all the other surfaces of a moving object, except the ends perpendicular to the direction of movement, using an electronic camera with a view to inspection and potential measurement of the surfaces. The invention also has the advantage of allowing such imaging using one single electronic camera, although two cameras can be used if desired, while the entire object is imaged by passing it once through an apparatus corresponding to the arrangement of the invention, given the substantially simultaneous imaging of all of the outer surfaces of the object by means of the invention. The invention has the further advantage of maintaining all the outer surfaces simultaneously within the depth of field of the electronic camera and also of eliminating the central perspective and replacing it with true planar projections. In addition, the apparatus implementing the arrangement of the invention has a compact and robust design and thus ensures excellent operational reliability.

BRIEF DESCRIPTION OF THE DRAWINGS

The invention is explained in further detail below with reference to the accompanying drawings.

FIG. 1 shows the device in a direction perpendicular to the direction of movement of a moving object, corresponding to direction I in FIG. 2, and FIG. 2 shows it accordingly in the direction of movement of the object, corresponding to direction II of FIG. 1.

FIGS. 3A-6A and 3B-6B illustrate separately the proceeding light beams in four viewing directions, with the directions perpendicular to each other.

FIGS. 3A, 3B show an arrangement for inspecting the lower surface of an object, FIGS. 4A, 4B an arrangement for inspecting the upper surface of an object, FIGS. 5A, 5B show an arrangement for inspecting a lateral side of an object and FIGS. 6A, 6B an arrangement for inspecting the other lateral side of the object.

DETAILED DESCRIPTION

Figure 1:
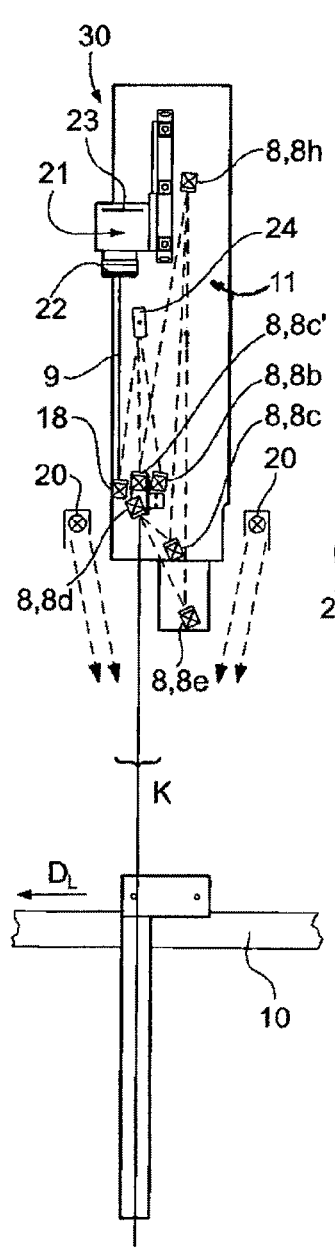
FIGS. 1 and 2 are schematic views of a preferred embodiment of the device of the invention for inspecting the open surfaces of an object from four viewing directions by using one single telecentric imaging unit comprising a video camera.

The figures illustrate a device for optical inspection of the open surfaces 1 of the profiles of objects 10, especially objects moving in the longitudinal direction, such as sawn goods or planed timber, but also objects of other materials, from at least two different viewing directions P1, P2. In this context, open surfaces 1 imply a surface visible from the outside and thus possible to inspect, but not e.g. the inside of pipes or hollow profiles, i.e. cavities. The open surfaces are generally referred to with reference numeral 1, which implies any open surface of an object, the specifying reference numerals implying the lateral surfaces 1c and 1d and the lower surface 1b and the upper surface 1a only in cases where it is necessary to make a difference between these. The objects move through the device of the invention in the direction of movement $D_L$. The device of the invention comprises primarily the illuminating means 20 for illuminating the open surfaces of the object. These illuminating means 20 may consist of any lamps emitting an adequate amount of light in a suitable wavelength range, possibly sources of diffused light or sources of directional light, which, however, emit incoherent radiation. Consequently, there are no other requirements on the light sources than those imposed on good general lighting, and they may be based on incandescent lamp techniques, fluorescence tube techniques, LED techniques (Light Emitting Diode) or any other similar, previously known or new techniques. Inspection of the open surfaces 1 of the objects 10 naturally requires the use of one or more specific illuminating wavelengths, which are, of course, used, the wavelength band of the illuminating radiation being broader or narrower, within the visible wavelength range, the infrared range, the ultraviolet range or the like. In this context, it is essential that there are no requirements regarding the parallel direction or coherence of the illuminating radiation, and hence there is no need for the use of one or more lasers in connection with the invention.

Figure 10:
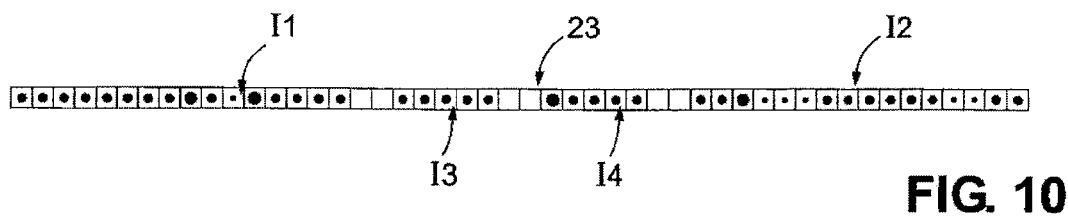
FIGS. 10 and 11 illustrate the principle of the image plane of the telecentric camera used in the invention including the light-sensitive pixels, in the case of a linear camera and a surface camera, respectively.
Figure 11:
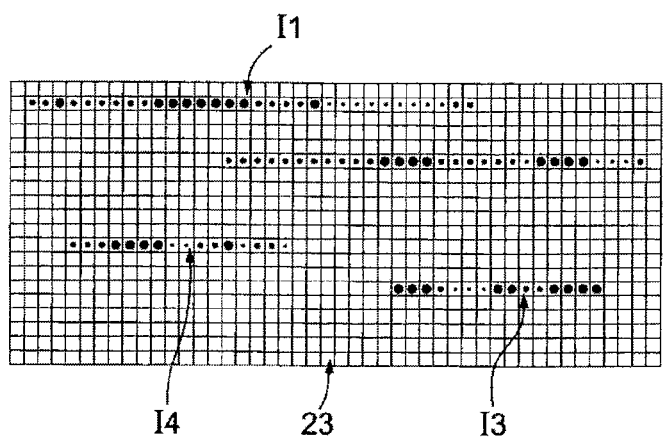

In addition, the device of the invention comprises sensor means 30 for detecting and converting into electric form the light intensity reflected from the different locations on the open surfaces 1 of the objects. In a preferred embodiment of the invention, the sensor means 30 consist of a first telecentric imaging unit 11, which consists of a non-telecentric camera 21 having an objective 22 and an image plane 23 formed of light-sensitive pixels and having an optical axis 9, and of a concave planar parabolic mirror 24 or possibly of a parabolic mirror in the focal plane F of which there is an aperture 25. The telecentric imaging unit 11 has an imaging area K in at least one plane. The imaging area K is formed by the joint effect of the image angle of the camera and a concave mirror—or a lens, respectively—located between this and the object, given the operation of the imaging unit with parallel beams outside the unit. The imaging area K is substantially in one plane when a linear camera is used, the type of image plane of this camera appearing in FIG. 10, however, there may also be provided an imaging area K in two different directions when a surface camera is used whose image plane type is shown in FIG. 11. Both of these have a real surface area, but a linear camera utilises primarily one dimension, whereas a surface camera utilises all the dimensions of the image plane. In the latter case as well, the imaging areas in different plane directions through different optical axes may be of different sizes, yet they are all covered by the name imaging area K in this description. Telecentric imaging units are commonly known and are thus not described in detail here. A telecentric imaging unit that is especially suitable for use in conjunction with this invention has been explained in the applicant's previous publication EP 1 089 106. In connection with the invention explained here, a telecentric imaging unit is preferably used, by means of which a non-telecentric camera is imparted telecentric properties by using a concave mirror, especially a concave strip mirror, and most advantageously a planar parabolic strip mirror, as has been explained in the reference mentioned above. It should be understood that there are no obstacles in terms of imaging theory to the use of a telecentric imaging unit of some other type, but such units can be used as well, provided that problems relating to costs and usability can be resolved. If a second telecentric imaging unit 12 is also used in this device, this second imaging unit 12 is of the same type as the first imaging unit 11 and thus comprises a non-telecentric camera 21, which consists of an objective 22 and an image plane 23 formed of light-sensitive pixels, and a concave planar parabolic mirror 24, with an objective aperture 25 in its focal plane F. Consequently, the telecentric imaging unit defined in this description relates both to the first imaging unit 11 and the second imaging unit 12.

In accordance with the invention, the device further comprises an angle mirror 13, which consists of two arms 3a and 3b, which are planar mirrors, preferably planar strip mirrors, as shown in FIGS. 1 and 3A-6A. The angle bisector 14 of the angle mirror 13 and the optical axis 9 of the telecentric imaging unit 11, 12, or the angle bisector 14 and the optical axes 9 of the telecentric imaging units 11, 12, respectively, are parallel, this definition comprising also the extensions of the angle bisector and the optical axis, as illustrated in FIGS. 2, 3B-6B and 7-9. The extensions are obvious, since turning the system into a physically different position by means of mirrors changes all the other features accordingly, and then the same conditions still are valid. In the most typical case, the angle bisector 14 of the angle mirror 13 and the optical axis 9 of the telecentric imaging unit 11, 12 or their extensions join, as can be seen in FIGS. 2, 3B-6B, 7 and 8. The device of the invention further comprises at least one first auxiliary mirror 8a within the imaging area K of the telecentric imaging unit and in addition, the object 10 is placed between the arms 3a, 3b of the angle mirror 13. If it is desirable to image and inspect all the open surfaces 1 of the object 10, especially the side surfaces 1c, 1d that have a dimension parallel with the optical axis 9 and the angle bisector 14, the object should be located in its totality within the area defined by the arms 3a, 3b of the angle mirror 13, the joint line of the upper edges 23 and the arms. If again, it is desirable to image and inspect only two opposite optical axes 9 and a surface having a dimension perpendicular to the angle bisector 14, i.e. an upper surface 1a and a lower surface 1b, it will be sufficient that the lower surface is within the area defined by the joint line of the upper edges 23 of the arms 3a, 3b of the angle mirror 13 or the joint plane J and the arms, because then the lower surface 1b is imaged via the arms of the angle mirror and the upper surface 1 directly to the telecentric imaging unit. The angle α between the arms 3a and 3b of the angle mirror is preferably 90°, as can be seen in the figures. The object 10 is preferably located between the arms 3a and 3b of the angle mirror in a manner such that it is within the area defined by the angle bisector 14 and one of the arms, either arm 3a or arm 3b. Then the lower surface 1b is imaged via both the arms of the angle mirror 13 and each of the side surfaces 1c and 1d is imaged via only one arm of the angle mirror, i.e. arm 3a or arm 3b. When the angle mirror 13 is used, the first viewing direction P1 oriented towards the lower surface 1, 1b of the object, i.e. viewed from the imaging unit to the rear side of the object 10, is formed via both the arms 3a and 3b of the angle mirror 13, as illustrated in FIGS. 1-9. The second viewing direction P2 oriented towards the upper surface 1, 1a of the object, i.e. to the front side of the object 10 viewed from the imaging unit, is formed without any angle mirror, because it can be directly seen. The third and fourth viewing direction P3, P4 oriented towards the lateral surfaces 1, 1c and 1, 1d of the object, i.e. to the sides of the object 10 viewed from the imaging unit, are both formed via one arm 3a or 3b of the angle mirror 13, as can be seen in FIGS. 1-9.

Further in accordance with the invention, the imaging direction $D_P$ parallel with the optical axis 9 of the telecentric imaging unit 11, 12 has been positioned or oriented with respect to the combination of the object 10 and the angle mirror 13, and the device comprises auxiliary mirrors 8 within the imaging area K of the telecentric imaging unit, between this and the object. The auxiliary mirrors are marked with the general reference numeral 8, which implies any special type of auxiliary mirror. The specifying reference numerals 8a-8i are used only when it is desirable to make a difference between the auxiliary mirrors used at different locations and/or in different positions. These auxiliary mirrors 8 are oriented and placed at such intervals from said telecentric imaging unit 11 and/or 12 that differences of imaging distance of the viewing directions P1 and/or P2 and/or P3 and/or P4 via the two arms 3a and 3b or one arm 3a or 3b or not via the arms of the angle mirror are compensated as they pass via said auxiliary mirrors. Imaging distances and routes of the viewing directions signify the distance of travel of a light beam forming the image from the surface of the object either 1} reflected directly via the auxiliary mirrors to a given location of the telecentric imaging unit or 2} reflected from the surface of the object via one arm of the angle mirror and via the auxiliary mirrors to the given location of the imaging unit mentioned above or 3} reflected from the surface of the object via the surfaces of two arms of the angle mirror and possibly via auxiliary mirrors to the given location of the telecentric imaging unit mentioned above. The difference of imaging distance naturally denotes the difference between the lengths measured along these different imaging distances or intervals. Thus, for instance, it can be understood from FIG. 7 that the imaging distance length m1 from the lower surface 1b of the object reflected via the two arms of the angle mirror is the longest one, the imaging distance length m3 from the first lateral surface 1d reflected via one arm of the angle mirror is slightly shorter, the imaging distance length m4 from one lateral surface 1c of the object reflected via the second arm of the angle mirror is still shorter and the imaging distance length m2 from the upper surface 1a of the object directly without any angle mirror is the shortest of all, when the imaging distance lengths are measured in the same transverse plane, in this case the joint plane J of the upper edges 23 of the angle mirror. The differences m1-m2, m1-m3 and m1-m4 between the imaging distances lengths are compensated with auxiliary mirrors and their location spacings.

Depending on the mutual position of the camera and the parabolic mirror 24 of the telecentric imaging unit and of the general direction of the telecentric imaging unit relative to the combination of angle mirror and object, the auxiliary mirrors can be disposed either individually or in couples along imaging distances corresponding to specific predetermined viewing directions P1 and/or P2 and/or P3 and/or P4, so that the image-generating light beams are reflected via them. The exact positions of the auxiliary mirrors depend on each application, an expert being capable of fixing them on the basis of the data provided in this text and the figures by general optical principles, so that they will not be explained in detail here. It is hence particularly essential to use an angle mirror 13 showing the rear side and the sides of the object 10, and auxiliary mirrors 8, which compensate for the differences in the imaging distance lengths above. The concave parabolic mirror or the planar parabolic mirror 24 and said auxiliary mirrors 8, 8a-8i, 18 are strip mirrors, whose reflective surfaces are transverse to the optical axis.

Figure 7:
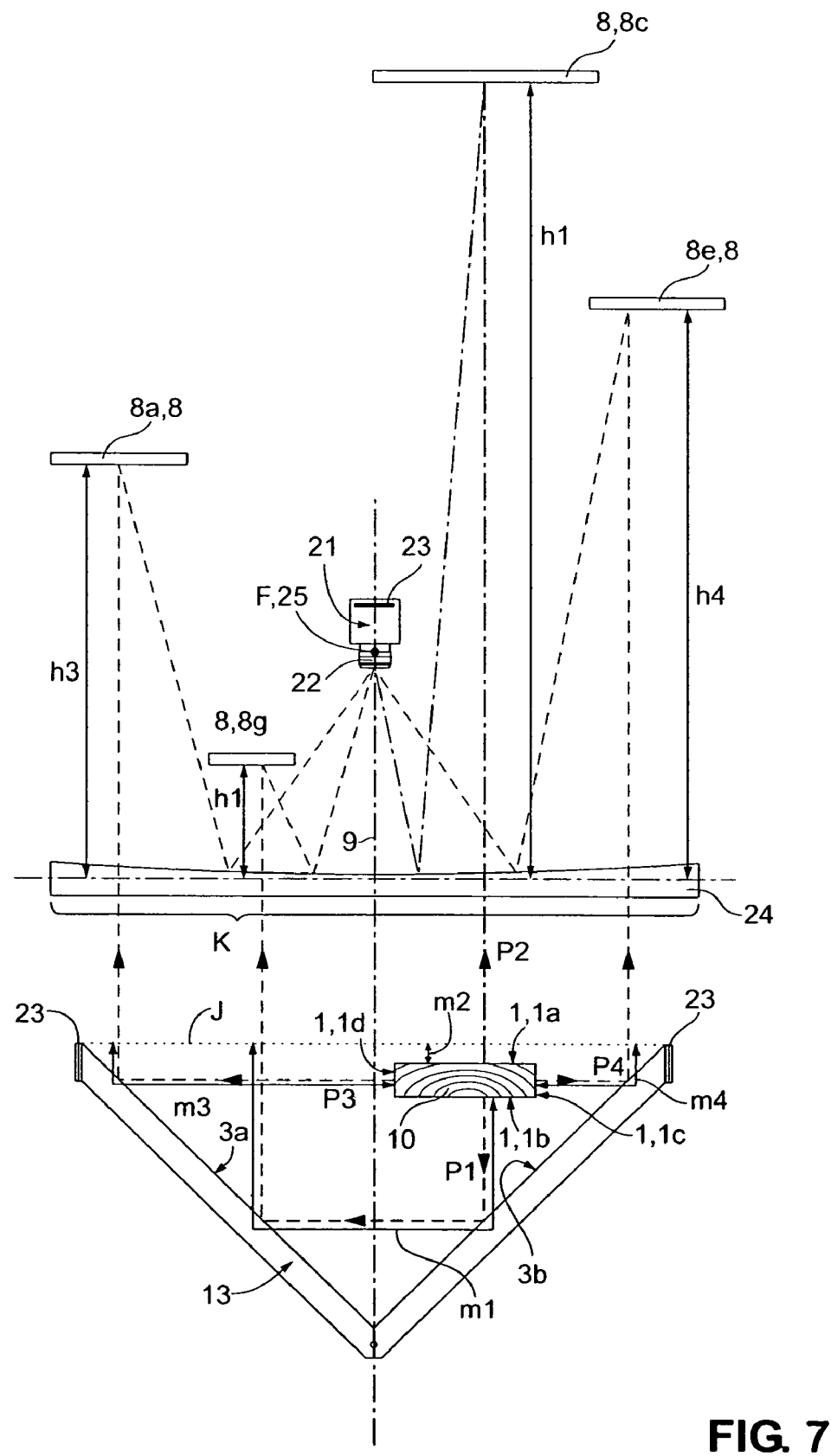
FIG. 7 is a schematic view of another embodiment of the device of the invention for inspecting the open surfaces of an object from four directions using one single telecentric imaging unit comprising a surface camera in the direction of movement of a moving object, i.e. in the same projection as in FIG. 2.

FIG. 7 illustrates one of the most straightforward embodiments of the invention, in which the concave planar parabolic mirror 24 faces towards the objective 22 and away from the combination of object and angle mirror. In this case, the device comprises at least a number of auxiliary mirrors 8 equalling the number of desired viewing directions of the object P1 and/or P2 and/or P3 and/or P4, at least one auxiliary mirror 8g, 8c, 8a, 8e being disposed for each viewing direction to reflect information from the object 10 to the telecentric imaging unit 11. Explained in detail, the image-generating light beams, i.e. the information from the object, follow the following imaging distances by reflection. Viewing direction P1 to the lower surface of the object. From the lower surface 1b via the two arms 3b and 3a of the angle mirror 13 to the auxiliary mirror 8g, which is located at only a small interval h1 from the planar parabolic mirror 24 and thus from the telecentric imaging unit 11, and via the auxiliary mirror of this to the imaging unit. Viewing direction P3 to the lateral surface of the object. From the lateral surface 1d via one arm 3a of the angle mirror 13 to the auxiliary mirror 8a, which is located at a greater interval h3 from the planar parabolic mirror 24 and thus from the telecentric imaging unit 11, and via the auxiliary mirror of this to the imaging unit. Viewing direction P4 to the lateral surface of the object. From the lateral surface 1c via the other arm 3b of the angle mirror 13 to the auxiliary mirror 8e, which is located at a still greater interval h4 from the planar parabolic mirror 24 and thus from the telecentric imaging unit 11, and via the auxiliary mirror of this to the imaging unit. Viewing direction P2 to the upper surface of the object. From the upper surface 1a to the auxiliary mirror 8c, which is at the greatest interval h2 from the planar parabolic mirror 24 and thus from the telecentric imaging unit 11, and via the auxiliary mirror of this to the imaging unit. The intervals h1, h2, h3 and h4 have been selected such that $2 \times h1 + m1 = 2 \times h2 + m2 = 2 \times h3 + m3 = 2 \times h4 + m4$, the telecentric imaging unit viewing all the sides of the object as located at the same interval.

Figure 8:
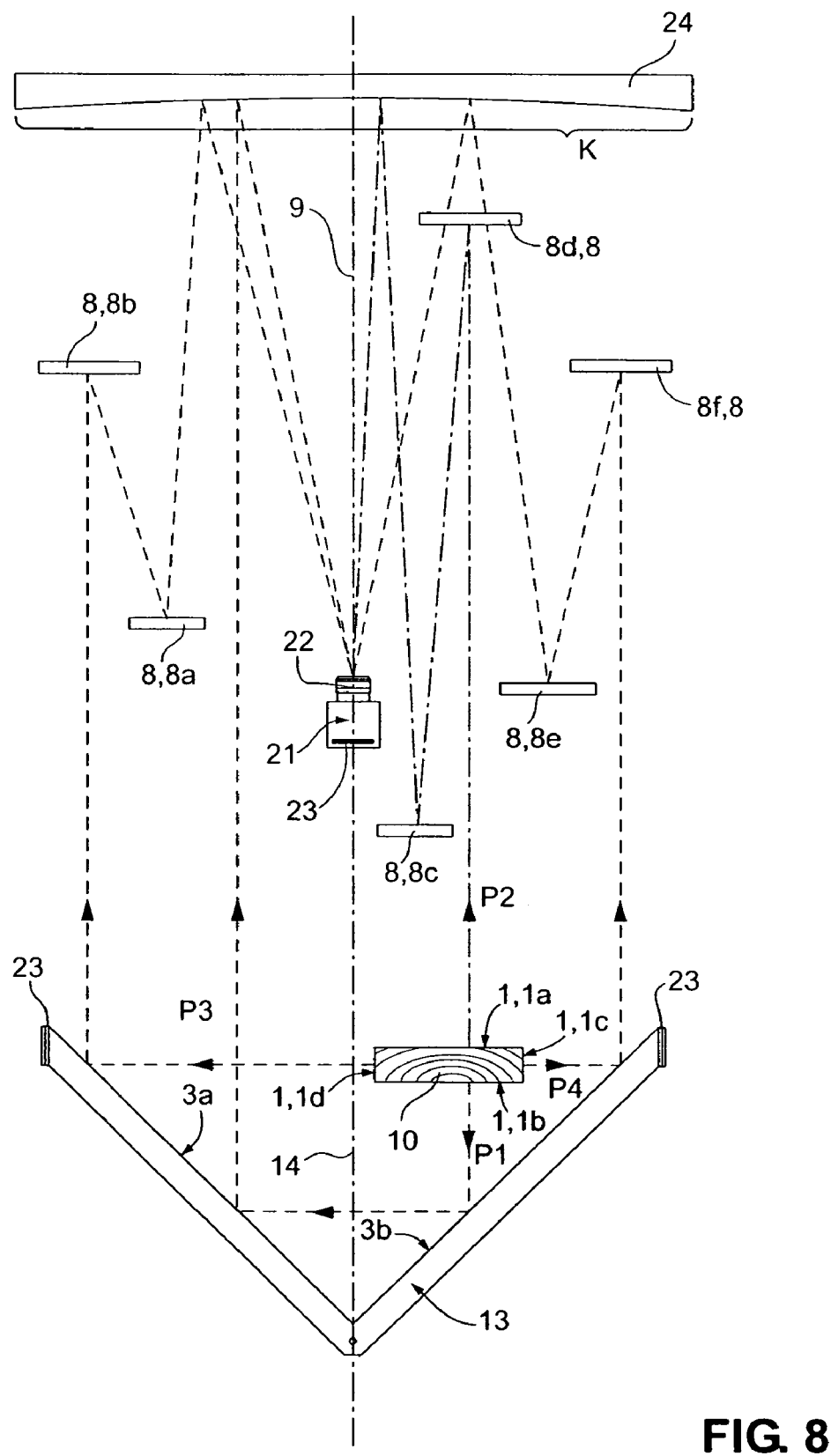
FIG. 8 is a schematic view of a third embodiment of the device of the invention for inspecting the open surfaces of an object from four directions using one single telecentric imaging unit, in the direction of movement of the object, i.e. in the same projection as in FIGS. 2 and 7.

FIG. 8 illustrates another embodiment of the invention, in which the concave planar parabolic mirror 24 faces towards the objective 22 and the combination of object and angle mirror. The device then comprises at least one pair of auxiliary mirrors 8a and 8b; 8c and 8d; 8e and 8f disposed for each desired viewing direction P2 and/or P3 and/or P4, which is shorter than the viewing direction P1 and/or P3 and/or P4 having the longest imaging distance, each pair of auxiliary mirrors being disposed to reflect information from the object 10 to the telecentric imaging unit. Explained in detail, the image-generating light beams, i.e. the information from the object, passes along the following imaging distances by reflection. Viewing direction P1 to the lower surface of the object. From the lower surface 1b via the two arms 3b and 3a of the angle mirror 13 directly to the telecentric imaging unit 11. Viewing direction P3 to the lateral surface of the object. From the lateral surface 1d via one arm 3a of the angle mirror 13 to the pair of auxiliary mirrors 8b and 8a—in this order—whose mutual interval is h5, and via this pair of auxiliary mirrors to the imaging unit. Viewing direction P4 to the lateral surface of the object. From the lateral surface 1c via the second arm 3b of the angle mirror 13 to the pair of auxiliary mirrors 8f and 8e—in this order—whose mutual interval h6 is greater, and via this pair of auxiliary mirrors to the imaging unit. Viewing direction P2 to the upper surface of the object. From the upper surface 1a to the pair of auxiliary mirrors 8d and 8c—in this order—whose mutual interval h7 is the greatest, via this pair of auxiliary mirrors to the imaging unit. The mutual intervals between the pairs of auxiliary mirrors h5, h6 and h7 have been selected such that $m1 = 2 \times h5 + m2 = 2 \times h6 + m3 = 2 \times h7 + m4$, the telecentric imaging unit viewing all the sides of the object as being at the same interval.

Figure 2:
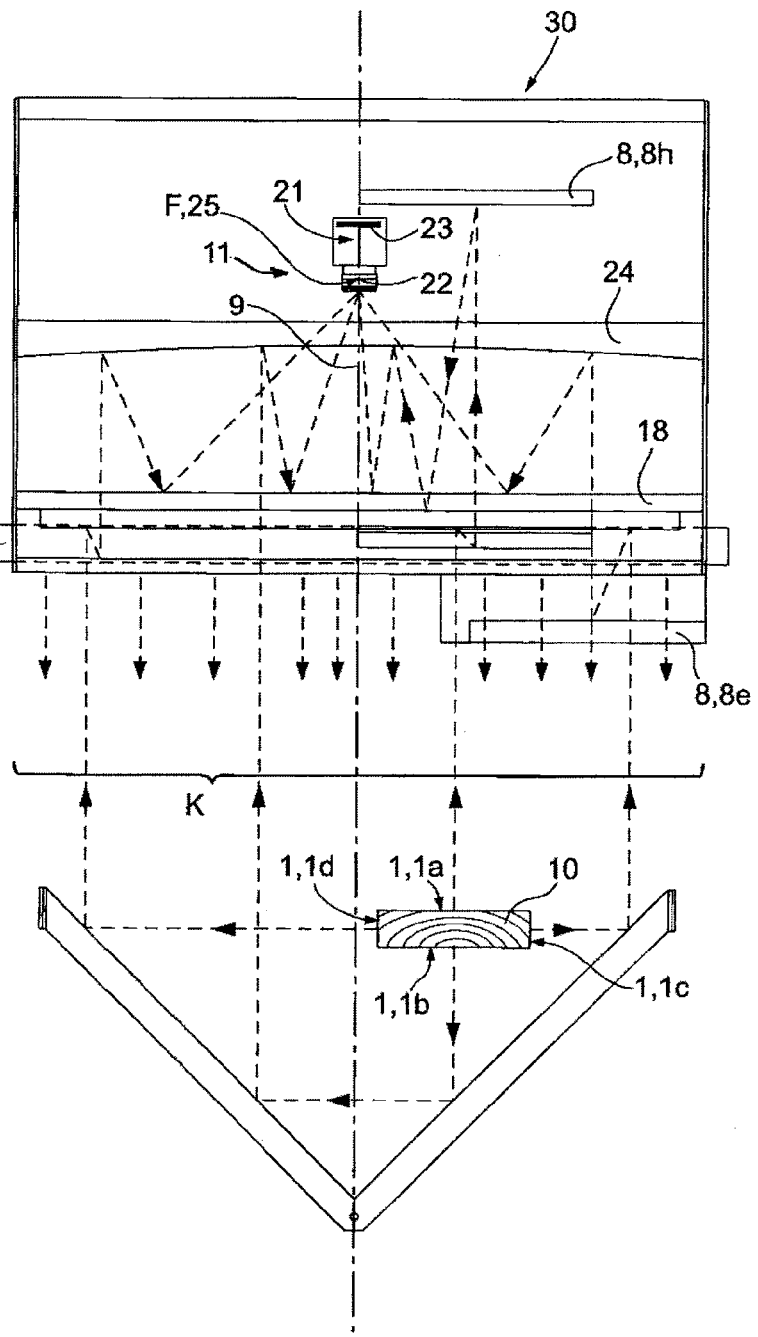

FIGS. 1 and 2 are general views of a preferred embodiment of the invention, in which a concave planar parabolic mirror 24 faces in the same direction as the objective 22 and towards the combination of object and angle mirror. For the sake of clarity, the information paths and mirror positions corresponding to the four viewing directions P1, P2, P3 and P4 of this embodiment are shown separately. Firstly, the device comprises an auxiliary mirror 18 in common for all the viewing directions placed between the planar parabolic mirror and the objective in order to reflect information from the planar parabolic mirror to said camera 21. In addition, the device comprises at least one pair of auxiliary mirrors 8a and 8b; 8e and 8b; 8d and 8c disposed for each desired viewing direction P2 and/or P3 and/or P4, which is shorter than the viewing direction P1 and/or P3 and/or P4 having the longest imaging distance, each pair of auxiliary mirrors being disposed to reflect information from the object 10 to the telecentric imaging unit. This embodiment may additionally comprise at least one additional pair of auxiliary mirrors 8h and 8i to lengthen the imaging distance corresponding to one or more viewing directions P1 and/or P2 and/or P3 and/or P4 by means of to-and-fro reflection between these. In the embodiment of the figures, these additional auxiliary mirrors 8h, 8i are located on a imaging distance corresponding to the second viewing direction P2, as can be seen in FIGS. 4A and 4B. Generally speaking, the additional pairs of auxiliary mirrors can be placed between the auxiliary mirrors and the information coming from the object, or between the auxiliary mirrors and the telecentric imaging unit, or between the auxiliary mirrors of the pairs of auxiliary mirrors, or between the pairs of auxiliary mirrors and the information from the object, or between the pairs of auxiliary mirrors and the telecentric imaging unit. Explained in detail, the image-generating light beams, i.e. the information from the object, passes along the following imaging distances by reflection. Viewing direction P1 to the lower surface of the object: From the lower surface 1b via the two arms 3b and 3a of the angle mirror 13 directly to the telecentric imaging unit 11, which consequently includes the common auxiliary mirror 18. Viewing direction P3 to the lateral surface of the object: From the lateral surface 1d via one arm 3a of the angle mirror 13 to the pair of auxiliary mirrors 8b and 8a—in this order—which have a mutual interval, and via this pair of auxiliary mirrors to the imaging unit. Imaging direction P4 to the lateral surface of the object: From the lateral surface 1c via one arm 3b of the angle mirror 13 to the pair of auxiliary mirrors 8b and 8e—in this order—whose mutual interval is greater, and via this pair of auxiliary mirrors to the imaging unit. Viewing direction P2 to the upper surface of the object: From the upper surface 1a first to the pair of auxiliary mirrors 8d and 8c—in this order—and from there to the pair of auxiliary mirrors 8h and 8i—in this order, which two pairs of auxiliary mirrors in total have the greatest mutual interval, and via these pairs of auxiliary mirrors to the imaging unit. The mutual intervals between the pairs of auxiliary mirrors and their positions have been selected such that the intervals shown in the figures meet the following conditions: $(l_{1.1}+l_{1.2})+l_{1.3}+l_{1.4}+l_{1.5}+l_{1.6}=(l_{2.1}+l_{2.2})+l_{2.3}+2\times l_{2.4}+l_{2.5}+l_{2.6}=l_{3.1}+l_{3.2}+l_{3.3}+l_{3.4}+l_{3.5}+l_{3.6}=l_{4.1}+l_{4.2}+l_{4.3}+l_{4.4}+l_{4.5}+l_{4.6}$, and then the telecentric imaging unit views all the sides of the object as being at the same interval.

The presentation above allows the conclusion that the imaging distances of the telecentric imaging unit 11 and 12 from the lower surface 1b, upper surface 1a and lateral surfaces 1c, 1d of the object to the telecentric imaging unit 11 have been disposed to be equal in the following manners. For the first viewing direction P1 from the lower surface 1, 1b of the object, this has been done by leaving out the auxiliary mirrors or by means of small mutual intervals between the auxiliary mirrors or pairs of auxiliary mirrors. For the second viewing direction P2 from the upper surface 1, 1a of the object, this has been done by means of great intervals between the auxiliary mirrors or pairs of auxiliary mirrors. For the third and fourth viewing directions P3, P4 from the lateral surfaces 1, 1c, 1d of the object, this has been done by means of mutual intervals between the auxiliary mirrors or pairs of auxiliary mirrors. We point out in this context that the invention is applicable both to inspection of the object 10 from all four viewing directions P1-P4 also to inspection of the object from three or only two different viewing directions, which three or two viewing directions may be any one of the four viewing directions mentioned above. Thus, if desired, the object can be inspected only with respect to its upper surface 1, 1a and to its lower surface 1, 1b. The choice of surface of the object to be inspected naturally depends on the nature of the object and its purpose of use, which are naturally selected by the user, i.e. which he knows and decides in advance. The device of the invention can be devised and constructed with all the four viewing directions available, although it has been decided in advance that some of them are not used, or in some cases a device of the invention can be devised and constructed so as to comprise means for implementing only two or three viewing directions P1 and/or P2 and/or P3 and/or P4. In this case, the design of the device will be simplified to the extent corresponding to the auxiliary mirrors or pairs of auxiliary mirrors corresponding to the excluded direction or directions.

The image plane 23 formed by the light-sensitive pixels of the camera 21 has dimensions for receiving at least two partial images I1 and/or I2 and/or I3 and/or I4, one of the partial images corresponding to one of the directions P1, P2, P3, P4 for inspecting the object. In other words, in accordance with the invention, all the viewing directions used generate simultaneously an image of the object on the image plane 23 of the camera or cameras. To this end, the image plane 23 formed by the light-sensitive pixels of the camera 21 has dimensions for receiving four partial images, each of which corresponds to one of the viewing directions P1, P2, P3, P4. The image plane 23 formed by the light-sensitive pixels of the camera 21 may have one dimension, i.e. length, the camera being a linear camera, and in that case the partial images I1 and/or I2 and/or I3 and/or I4 are disposed by means of auxiliary mirrors and/or pairs of auxiliary mirrors in alignment as illustrated in FIG. 10. Since the image plane 23 may optionally have a dimension in two mutually perpendicular directions, i.e. length and width, in the case of a surface camera, the partial images I1 and/or I2 and/or I3 and/or I4 can be disposed by means of auxiliary mirrors and/or pairs of auxiliary mirrors either exactly aligned or slightly overlapping as shown in FIG. 11.

Figure 9:
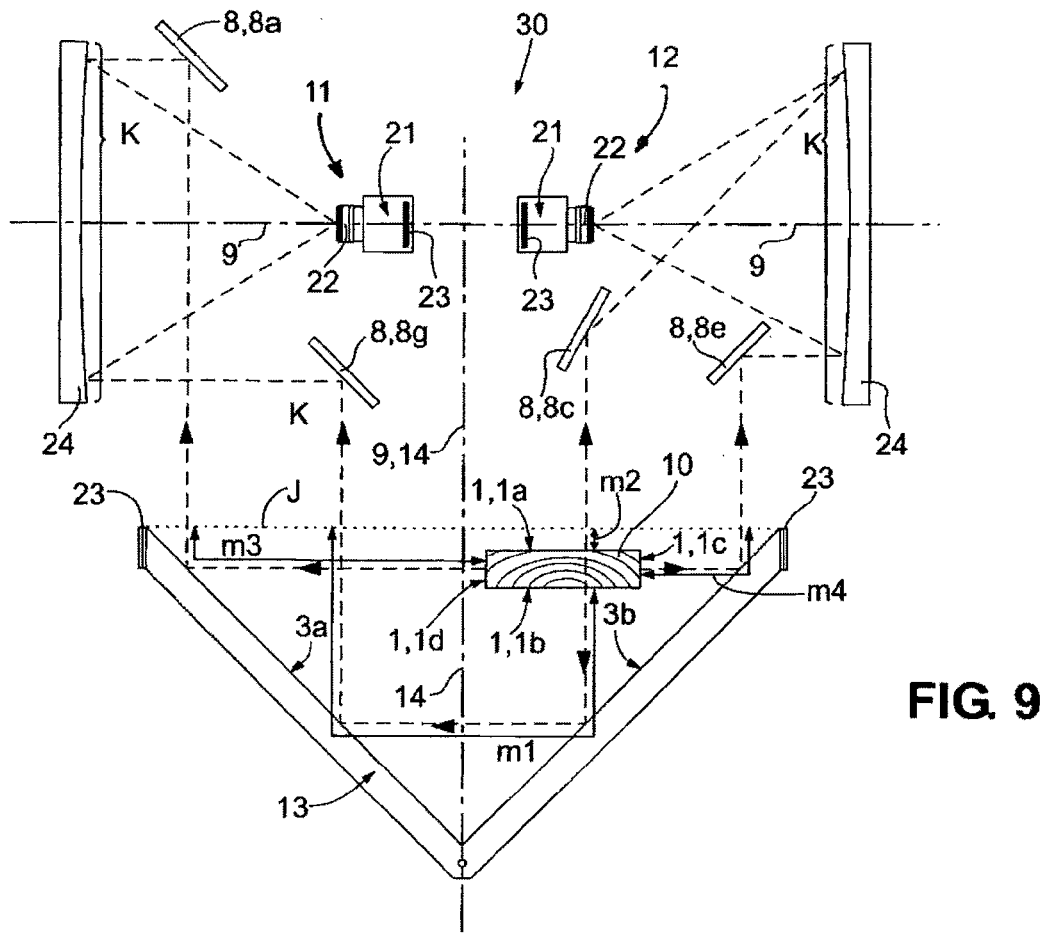
FIG. 9 is a schematic view of a fourth embodiment of the device of the invention for inspecting the open surfaces of an object from four directions using two telecentric imaging units, in the direction of movement of the object, i.e. in the same projection as in FIGS. 2, 7 and 8.

The device of the invention may comprise also a second telecentric imaging unit 12, which comprises a non-telecentric camera 21, which consists of an objective 22 and an image plane 23 formed of light-sensitive pixels, and a concave planar parabolic mirror 24, with the objective aperture 25 located in the focal plane F of this. Hence this second imaging unit 12 is of the same type as the first imaging unit 11. Each of the first and second telecentric imaging unit receives an image from at least two viewing directions P1 and/or P2 and/or P3 and/or P4 following the principles explained above in this description. FIG. 9 illustrates such a case of two telecentric imaging units 11 and 12. Regarding the array of auxiliary mirrors 8, the embodiment of FIG. 9 is on principle of the same type as the embodiment of FIG. 8, with only images of the lower surface and one lateral surface of the object being reflected to the first imaging unit 11, while the images of the upper surface and the second lateral surface are reflected to the second imaging unit 12. However, in this case, the differences between the imaging distance lengths caused by the angle mirror as explained above have to be compensated only per one single telecentric imaging unit. In other words, only two imaging distance lengths m1 and m3 need to be compensated with respect to each other and two other imaging distance lengths m2 and m4 need to be compensated only with respect to each other. We also point out with respect to this embodiment that, in this case as well, the telecentric imaging units 11, 12 are directed towards the combination of object and angle mirror, but with the orientation performed by reflection via the auxiliary mirrors 8a, 8g, 8c and 8e in an inclined position. The angle bisector 14 of the angle mirror 13 and the optical axes 9 of the telecentric imaging units 11, 12, more precisely their extensions in this case, are also aligned, and the angle bisector 14 and the optical axes join, because the two imaging units have been turned by and angle and the auxiliary mirrors turn all the optical features by exactly the same angle.

While there have been shown and described and pointed out fundamental novel features of the invention as applied to preferred embodiments thereof, it will be understood that various omissions and substitutions and changes in the form and details of the devices and methods described may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto. Furthermore, in the claims means-plus-function clauses are intended to cover the structures described herein as performing the recited function and not only structural equivalents, but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed is:

1. A device for optical inspection of open surfaces of an object from at least two different viewing directions, the device comprising:
an illumination source for illuminating the open surfaces of the object,
a sensor for detecting the light intensity reflected by different locations of the open surfaces of the object and for converting it into electric form,
the sensor in the device comprising at least a first telecentric imaging unit having an optical axis; and
an angle mirror and auxiliary mirrors within an imaging area of the telecentric imaging unit, between the telecentric imaging unit and the object;
the device configured so that the object is positioned between the arms of the angle mirror the telecentric imaging unit is directed towards a combination of the object and the angle mirror, and said auxiliary mirrors are oriented and placed at intervals from said telecentric imaging unit that differences of imaging distances of light beams between the viewing directions from the surfaces of the object to the telecentric imaging unit are compensated with respect to imaging distance lengths as the light beams pass via said auxiliary mirrors.

2. A device as defined in claim 1, wherein said illumination source are diffused light sources or directional light sources, which emit incoherent radiation.

3. A device as defined in claim 1, wherein the angle bisector of the angle mirror and said optical axis or their extensions are aligned; and that said angle bisector and said optical axis join.

4. A device as defined in claim 3, wherein the concave plane-parabolic mirror faces towards the objective and away from the combination of the object and the angle mirror; and that the device comprises at least such number of auxiliary mirrors equalling the number of desired viewing directions towards the object, whereupon at least one auxiliary mirror is disposed for each viewing direction to reflect information from the object to the telecentric imaging unit.

5. A device as defined in claim 4, wherein it further comprises at least one additional pair of auxiliary mirrors to lengthen the imaging distance corresponding to one or more viewing directions by means of to-and-fro reflection between these auxiliary mirrors; and that the additional pair(s) of auxiliary mirrors are placed:
between the auxiliary mirrors and the information coming from the object, or
between the auxiliary mirrors and the telecentric imaging unit, or
between the auxiliary mirrors of the pairs of auxiliary mirrors, or
between the pairs of auxiliary mirrors and the information coming from the object, or
between the pairs of auxiliary mirrors and the telecentric imaging unit.

6. A device as defined in claim 3, wherein the concave plane-parabolic mirror faces towards the objective and towards the combination of the object and the angle mirror; that the device comprises at least one pair of auxiliary mirrors disposed for each such desired viewing direction that is shorter than the viewing direction having the longest imaging distance; and that each pair of auxiliary mirrors is disposed to reflect information from the object to the telecentric imaging unit.

7. A device as defined in claim 3, wherein the concave plane-parabolic mirror faces in the same direction as the objective and towards the combination of the object and the angle mirror; that the device comprises an auxiliary mirror in common for all of the viewing directions located between the plane-parabolic mirror and the objective to reflect information from the plane-parabolic mirror to said camera, and at least one pair of auxiliary mirrors is disposed for each such desired viewing direction that is shorter than the viewing direction having the longest imaging distance; and that each pair of auxiliary mirrors is disposed to reflect information from the object to the telecentric imaging unit.

8. A device as defined in claim 1, wherein the first telecentric imaging unit comprises:
a non-telecentric camera having an objective and an image plane formed of light-sensitive pixels, and
a concave plane-parabolic mirror, with an aperture of the objective located in the focal plane of said mirror.

9. A device as defined in claim 1, wherein said concave plane-parabolic mirror and said auxiliary mirrors are strip mirrors, whose reflective surfaces are transverse to the optical axis and which are disposed each in a different manner so laterally off the optical axis that all of the viewing directions to a lower surface, upper surface and lateral surfaces of the object are simultaneously available without mutual shading between the auxiliary mirrors.

10. A device as defined in claim 1, wherein the imaging distances from a lower surface, upper surface and lateral surfaces of the object to the telecentric imaging unit have been disposed with equal lengths:
for a first viewing direction from the lower surface of the object without auxiliary mirrors or with small mutual intervals between the auxiliary mirrors or pairs of auxiliary mirrors,
for a second viewing direction from the upper surface of the object with long mutual intervals between the auxiliary mirrors or pairs of auxiliary mirrors,
for a third and a fourth viewing direction from the lateral surfaces of the object with medium mutual intervals between the auxiliary mirrors or pairs of auxiliary mirrors.

11. A device as defined in claim 1, wherein the object is disposed within the area defined by an angle bisector and one arm of the angle mirror.

12. A device as defined in claim 1, wherein the angle between the arms of the angle mirror is 90°.

13. A device as defined in claim 1, wherein the image plane formed by the light-sensitive pixels of the camera has a length and/or width for receiving at least two partial images, each of which corresponds to one of the viewing directions.

14. A device as defined in claim 1 further comprising a second telecentric imaging unit comprising:
a non-telecentric camera having an objective and an image plane formed of light-sensitive pixels, and
a concave plane-parabolic mirror, with an aperture of the objective located in the focal plane of this device, and that both the first and the second telecentric imaging unit receive an image at least from two viewing directions.

15. A device as defined in claim 1, wherein said compensation reduces said differences in imaging distance lengths to zero.

16. A device for optical inspection of open surfaces of an object from at least two different viewing directions, the device comprising:
means for illuminating the open surfaces of the object,
means for detecting the light intensity reflected by different locations of the open surfaces of the object and for converting it into electric form,
said means for detecting comprising at least a first telecentric imaging unit having an optical axis; and an angle mirror and auxiliary mirrors within an imaging area of the telecentric imaging unit, between the telecentric imaging unit and the object;

the device configured so that the object is positioned between the arms of the angle mirror, the telecentric imaging unit is directed towards a combination of the object and the angle mirror, and said auxiliary mirrors are oriented and placed at such intervals from said telecentric imaging unit that differences of imaging distances of light beams between the viewing directions from the surfaces of the object to the telecentric imaging unit are compensated with respect to imaging distance lengths as the light beams pass via said auxiliary mirrors.

17. A device as defined in claim 16, wherein said means for illuminating are diffused light sources or directional light sources, which emit incoherent radiation.

18. a device as defined in claim 16, wherein said compensation reduces said differences in imaging distance lengths to zero.

* * * * *